US009119770B2

(12) United States Patent
Reynolds et al.

(10) Patent No.: US 9,119,770 B2
(45) Date of Patent: Sep. 1, 2015

(54) RECONSTITUTION DEVICE

(75) Inventors: David L. Reynolds, Bromont (CA);
Daniel MacDonald, Brossard (CA); Yan Tremblay, Orford (CA); Eric Geoffroy, Montreal (CA); Mathieu Viens, Granby (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 38 days.

(21) Appl. No.: 13/261,792

(22) PCT Filed: Jul. 5, 2012

(86) PCT No.: PCT/CA2012/000650
§ 371 (c)(1),
(2), (4) Date: Dec. 16, 2013

(87) PCT Pub. No.: WO2013/003951
PCT Pub. Date: Jan. 10, 2013

(65) Prior Publication Data
US 2014/0284354 A1    Sep. 25, 2014

(30) Foreign Application Priority Data

Jul. 6, 2011 (CA) ...................................... 2745320

(51) Int. Cl.
*A61J 1/20* (2006.01)
*A61K 31/137* (2006.01)
*A61K 31/5575* (2006.01)
*B65D 81/32* (2006.01)

(52) U.S. Cl.
CPC ............. *A61J 1/2093* (2013.01); *A61K 31/137* (2013.01); *A61K 31/5575* (2013.01); *B65D 81/3211* (2013.01); *A61J 2001/2031* (2013.01); *A61J 2001/2051* (2013.01); *A61J 2200/40* (2013.01); *A61J 2200/72* (2013.01)

(58) Field of Classification Search
CPC ............ B65D 81/3211; B65D 81/3205; A61J 1/2093
USPC ........ 222/145.1, 386, 136, 325–327; 220/501
See application file for complete search history.

(56) References Cited

U.S. PATENT DOCUMENTS

| | | | | |
|---|---|---|---|---|
| 5,398,847 A | * | 3/1995 | Hasegawa | 222/41 |
| 5,921,167 A | * | 7/1999 | Giesy et al. | 92/172 |
| 7,237,693 B2 | * | 7/2007 | Brennan et al. | 222/327 |
| 7,497,355 B2 | * | 3/2009 | Horner et al. | 222/137 |
| 2006/0178644 A1 | * | 8/2006 | Reynolds | 604/232 |
| 2008/0054001 A1 | * | 3/2008 | Roth et al. | 220/502 |

(Continued)

FOREIGN PATENT DOCUMENTS

EP    1093826 A1 *    4/2001

*Primary Examiner* — Donnell Long
(74) *Attorney, Agent, or Firm* — Eric Fincham (57) ABSTRACT

A reconstitution device (10) for mixing a first component (70) with a second component (72) wherein there are provided first and seconds housings (12, 14) which are engageable together, a conduit (28) having an internal passageway (30) having a dispensing end and an inlet end, first, second and third plungers (52, 54) mounted in said internal passageway (30), first and second compartments (70, 72) being defined by the plungers, a shearing channel (32) formed in a side wall of conduit (28) to permit mixing of contents located in the first and second compartments (74, 76), a plunger rod (58) to cause initial mixing of the first and second components (70, 72), and a spring member (48) biasing against the moveable member (42).

14 Claims, 9 Drawing Sheets

(56) References Cited

U.S. PATENT DOCUMENTS

2008/0230565 A1* 9/2008 Hohmann et al. ............ 222/386
2011/0166596 A1* 7/2011 Delmotte ...................... 606/214
2012/0206992 A1* 8/2012 Stewart ......................... 366/130
2012/0215205 A1* 8/2012 Alvey et al. ................... 604/516

* cited by examiner

RECONSTITUTION DEVICE

FIELD OF THE INVENTION

The present invention relates to a reconstitution device or apparatus and a method for reconstituting and more particularly, relates to reconstitution devices suitable for reconstituting many different materials. Furthermore, the present invention includes methods of treatment and methods of use related to a reconstitution device or apparatus.

BACKGROUND OF THE INVENTION

In the pharmaceutical industry, the step of reconstituting a drug or other material is well known. Many pharmaceutical compositions are not capable of being stored for extended periods of time since their potency may change. In order to overcome this problem of a short shelf life, such pharmaceutical products are stored as a solid component and a liquid component. Prior to use, the two components must be mixed together.

Furthermore, while preservatives are effective in preserving some ingredients included in a pharmaceutical composition, such preservatives may cause adverse reactions with other ingredients of the pharmaceutical composition, namely the active ingredient, and result in degradation and/or spoilage. In some situations, refrigeration may be used to combat degradation or spoilage of a pharmaceutical composition. However, refrigeration is not always accessible and administration of a cooled pharmaceutical composition may reduce the effectiveness, namely solubility and penetration, of the pharmaceutical composition.

Although many reconstitution systems are directed for use with a powdered solid component and a diluent component, there are also occasions when other forms of material may be utilized. Thus, the reconstitution system may employ two liquids, or a semi liquid component such a paste along with a second component which is typically a liquid. Several problems must be addressed in any reconstitution device such as the problem of obtaining a proper mixture. For highly soluble products such as a powder and a diluent therefore, a simple mixing of the two components is sufficient. Typically in such an arrangement, the diluent and dry components are stored in separate compartments of a device. The device will include a by-pass such that pressure on a plunger will cause the liquid to go through the by-pass to mix with the dry ingredient. Usually a simple shaking of the mixture is sufficient to assure that the mixture is properly constituted.

However, certain pharmaceutical products require a more thorough mixing and the conventional devices cannot be used. One other problem which is frequently encountered is that the components to be mixed are utilized in a small quantity and conventional mixing devices are not suitable. This is particularly the case when one of the components is in the form of a paste into which a liquid like constituent must be mixed.

Furthermore, poor application of a pharmaceutical composition can hinder the effectiveness of the pharmaceutical composition. Some advances in the ergonomics and delivery of pharmaceutical compositions have been made, see for example U.S. Pat. No. 6,224,573 (Yeager et al.). However, previous applicators that combined more than one composition together prior to administration do not have sufficient mixing mechanisms to achieve optimal composition storage, mixing, and application. Thus, there remain needs for methods of treating and devices to overcome all the issues that remain with the storage, mixing, and administration of pharmaceutical compositions.

SUMMARY OF THE INVENTION

It is an object of the present invention to provide a reconstitution system or device which is suitable for reconstituting small amounts of pharmaceutical compounds.

It is a further object of the present invention to provide methods for the reconstitution of pharmaceutical compounds. Some embodiments are suitable for reconstituting small amounts of pharmaceutical compositions.

According to one aspect of the present invention, there is provided a reconstitution device comprising a device suitable for mixing a first component with a second component, the device comprising first and second housings, the first and second housings being engageable together, a conduit having an internal passageway formed in the first housing, the internal passageway having a dispensing end and an inlet end, a first plunger mounted in the internal passageway proximate the dispensing end, a second plunger mounted in the internal passageway proximate the inlet end, a third plunger mounted in the internal passageway intermediate the first and second plungers, the first and third plungers defining a first compartment therebetween, the second and third plungers defining a second compartment therebetween, a plunger rod at least partially within the internal passageway at the inlet end, a moveable member located in the second housing, the moveable member engaging the first plunger, and a shearing channel formed in a side wall of the conduit to permit mixing of contents located in the first and second compartments.

According to a further aspect of the present invention, there is also provided a device for mixing a first component with a second component, the device comprising first and second housings, the first and second housing each having a partial screw thread formed on an exterior surface thereof, the first and second housings being engageable together by means of the screw threads, a conduit having an internal passageway formed in the first housing, the internal passageway having a dispensing end and an inlet end, a first plunger mounted in the internal passageway proximate the dispensing end, a second plunger mounted in the internal passageway proximate the inlet end, a third plunger mounted in the internal passageway intermediate the first and second plungers, the first and third plungers defining a first compartment therebetween, the second and third plungers defining a second compartment therebetween, a plunger rod at least partially within the internal passageway at the inlet end, a moveable member located in the second housing, the moveable member engaging the first plunger, the moveable member having at least one leg extending upwardly therefrom, the upwardly extending leg engaging the first housing such that the first and second housing cannot be disengaged from an initial first position, the arrangement being such that when the plunger rod is moved to commence transfer from the second compartment to the first compartment, the leg on the moveable member disengages from the first housing to permit rotatable movement of the first and second housings.

According to a still further aspect of the present invention, there is also provided a method of filling a reconstitution device comprising the steps of supplying first and second housings, the first and second housings being engageable together, a conduit having an internal passageway formed in the first housing, the internal passageway having a dispensing end and an inlet end, a moveable member mounted in the second housing, placing a first plunger on the moveable member, the plunger sealing the dispensing end of the internal passageway, inserting a first material in the internal passageway on the first plunger, inserting a second plunger in the internal passageway from the inlet end to seal the first material in a first compartment formed between the first and second plungers, placing a second material on top of the second plunger, inserting a third plunger to seal the second material between the second and third plungers, and placing a plunger rod adjacent the third plunger.

In one embodiment, the device, as above mentioned, includes first and second housings. The first and second housings are engageable together such that they may be retained in the assembled position for a period of time as will be discussed hereinbelow. The first and second housings are releasable.

Within one of the housings, there is provided a conduit having a hollow passageway therein. The passageway has three plungers mounted therein for containing the ingredients to be reconstituted. In one embodiment, there is provided a first plunger which is located proximate the outlet or dispensing end of the conduit as will be discussed in greater detail hereinbelow. A second plunger is mounted in the internal passageway closer to the inlet end of the conduit. However, this second plunger is not located at the very end, but rather is usually proximate the middle of the conduit.

A third plunger mounted in the passageway is intermediate of the first and second plungers. The first and third plungers define a first compartment for receiving a first ingredient while the second and third plungers define a second compartment therebetween for containing a second ingredient. Typically, the second compartment will contain the less viscous of the ingredients. A shearing channel is formed in the side wall of the conduit, again for reasons which will be discussed hereinbelow. The shearing channel is initially at least partially covered by the third plunger so as to maintain the ingredients apart.

A plunger rod is utilized to exert pressure or push on the second plunger. This results in movement of the third plunger such that access to the shearing channel is obtained. Subsequently, the ingredient in the second compartment will pass through the shearing channel to mix with the component in the first compartment.

In one embodiment, a spring member is provided which is arranged to exert pressure or bias the first plunger. Thus, after transferring the ingredient from the second compartment to the first compartment, a mixture or admixture is achieved. Subsequently, with release of the pressure on the plunger rod, the spring will cause the first plunger to move rearwardly such that the mixture or admixture is again forced to pass through the shearing channel. This can be repeated several times to ensure that the composition formed by the at least two ingredients is properly mixed. Naturally, one could use the finger of the user instead of the spring.

To assist in proper mixing, the shearing channel is sized to provide a relatively small cross-sectional area such that significant shearing is obtained. Typically, the shearing channel will have a diameter of less than 1 mm. In alternative embodiments, the diameter of the shearing channel is greater than 1 mm, less than 1 mm, 0.5 mm, or 0.3 mm. In other embodiments, the shearing channel does not have a fixed diameter; rather, the shearing channel is tapered.

As previously mentioned, the device is particularly suited for mixing of small amounts. In some instances, the total volume of the constituents would range between 0.1 and 0.2 of a cc. In alternative embodiments, the total volume is greater than 10 cc, less than 10 cc, 5 cc, 1 cc, or 0.5 cc.

The moveable member mounted in the second housing in one embodiment is connected to the first plunger. In order to do so, the moveable member has a small rod like element with an enlarged end in some embodiments. The enlarged end would enter the plunger such that the plunger will move back and forth with the moveable member.

The plunger rod is positioned to initially contact the second plunger. Thus, a portion of the plunger fits within the passageway while a further portion extends to the end of the housing which is open and thus forms a head for applying pressure to the plunger rod by the thumb or a finger of the user.

To prevent accidental movement of the plunger rod, the head is retained in position by a projection on the interior wall of the housing. The projection is sufficient to maintain the plunger rod in position until sufficient pressure is applied to the head.

Once the initial pressure is applied to the plunger rod, it will start moving the second plunger downwardly and apply pressure to the ingredient in the second compartment. This in turn will cause sufficient movement of the third plunger such that access is had to the shearing channel. The liquid will then mix with the ingredient in the first compartment. Upon releasing the plunger rod, the spring will apply sufficient pressure to the moveable member which in turn will move the first plunger rearwardly and force the mixture to again pass through the shearing channel. In some embodiments, these steps are repeated. Instead of using the spring to move the moveable member, a manual arrangement wherein a digit of the user may be employed.

In one embodiment, the initial movement of the third plunger will cause the disengagement of the first and second housings to thereby permit the housings to be disengaged when so desired. This arrangement provides the advantage that the user cannot access the ingredients without at least having gone through one mixing operation.

The present invention also includes methods of reconstitution and methods of treatment with reconstituted compositions, namely pharmaceutical compositions. Although the some embodiments have compositions for reconstitution and use for treatment are pharmaceutical compositions suitable for the treatment of sexual dysfunction, the methods disclosed herein are suitable for other compositions, such as cosmetics, foods, and vaccines.

BRIEF DESCRIPTION OF THE DRAWINGS

Having thus generally described the invention, reference will be made to the accompanying drawings illustrating embodiments thereof, in which.

DETAILED DESCRIPTION OF THE INVENTION

Definitions

Unless otherwise stated, the following terms used in this application, including the specification and claims, have the definitions given below. As used in the specification and the appended claims, the singular forms "a", "an", and "the" include plural referents unless the context clearly dictates otherwise.

The term "administer" or "administration" means the act of giving a pharmaceutical composition to a subject.

The term "compound", "composition", "ingredient", and "component" may sometimes be used interchangeably to refer one or more chemical components.

"Disease" means any disease, condition, symptom, or indication.

The term "drug" or "pharmaceutically active agent" as used herein is intended to mean a compound or composition of matter which, when administered to an organism/subject, which is human or animal, induces a desired pharmacologic and/or physiologic effect by local and/or systemic action.

An "effective amount" means an amount of a compound that, when administered to a subject for treating a disease, is sufficient to effect such treatment for the disease or condition. The "effective amount" will vary depending on the compound, the disease state being treated, the severity or the disease being treated, the age and relative health of the subject, the route and form of administration, the judgment of the attending medical or veterinary practitioner and other factors.

As used herein "excipient" means a component or an ingredient that is acceptable in the sense of being compatible with the other components of the formulation and not deleterious to a subject to which the formulation is to be administered.

The term "immediately before" or "immediately prior" generally means less than two hours before application of a composition or before the desired next step; however, this term is not limited to this time frame because the chemical properties or desired state of a pharmaceutical composition may require a time frame more than two hours before proceeding with the next step.

The term "immediately after" or "immediately following" generally means less than two hours after application of a composition before the desired next step; however, this term is not limited to this time frame because the chemical properties or desired state of a pharmaceutical composition may require a time frame more than two hours before proceeding with the next step.

"Optional" or "optionally" means that the subsequent described event or circumstance may but need not occur, and that the description includes instances where the event or circumstances occurs and instances in which it does not occur.

The term "penetration enhancer" means a chemical compound that increases the permeability of the skin to a drug.

"Pharmaceutical compositions" means a composition that is generally safe, non-toxic, and neither biologically nor otherwise undesirable and includes that which is actable for veterinary as well as human pharmaceutical use.

"Pharmaceutically acceptable" means that which is useful in preparing a pharmaceutical composition that is generally safe, non-toxic, and neither biologically nor otherwise undesirable and includes that which is actable for veterinary as well as human pharmaceutical use. This language may also include pharmaceutically acceptable salts of a pharmaceutically acceptable composition.

"Subject" means mammals and non-mammals and the term does not denote a particular age or sex.

The term "pharmacological effect" as used herein encompasses effects produced in the subject that achieve the intended purpose of a therapy.

"Transdermal" application or drug delivery means delivery of a drug by passage into and though the skin and/or the underlying tissues and into the blood stream.

"Treating" or "treatment" of a disease includes preventing the disease, inhibiting the disease, and/or relieving the effects of a disease.

The methods and apparatuses disclosed herein can be used in the mixing and/or application of numerous different compositions, including vaccines, medicaments, pharmaceutical compositions, cosmetics, and food products. Although the some embodiments include applications and methods for pharmaceutical compositions, one skilled in the art will appreciate applicability of this disclosure in other areas.

Referring to the drawings in greater detail and by reference characters thereto, there is illustrated a reconstitution device which is generally designated by reference numeral 10.

Figures 1, 2, 3:
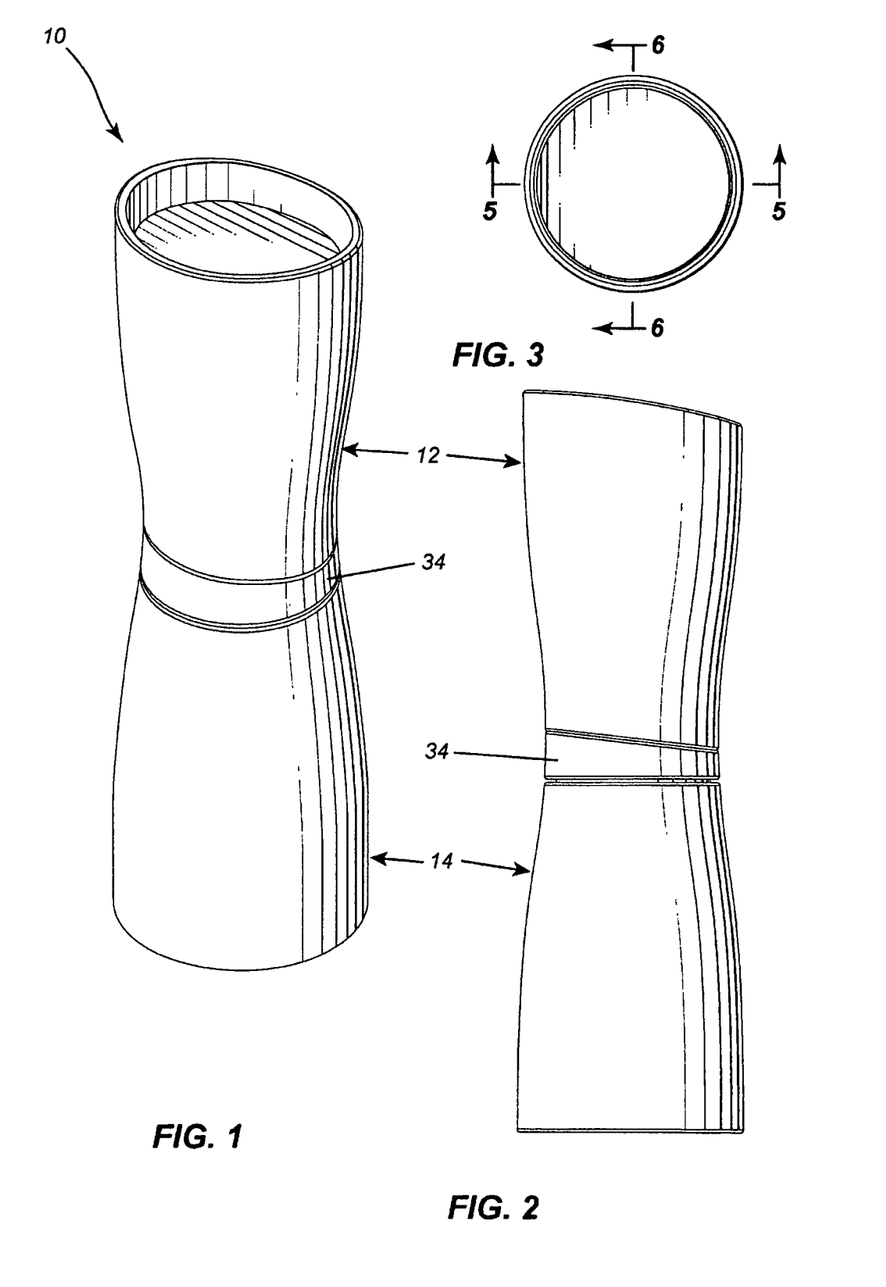
FIG. 1 is a perspective view of a reconstitution device according to an embodiment of the present invention.
FIG. 2 is a side elevational view thereof.
FIG. 3 is a top plan view thereof.
Figure 4:
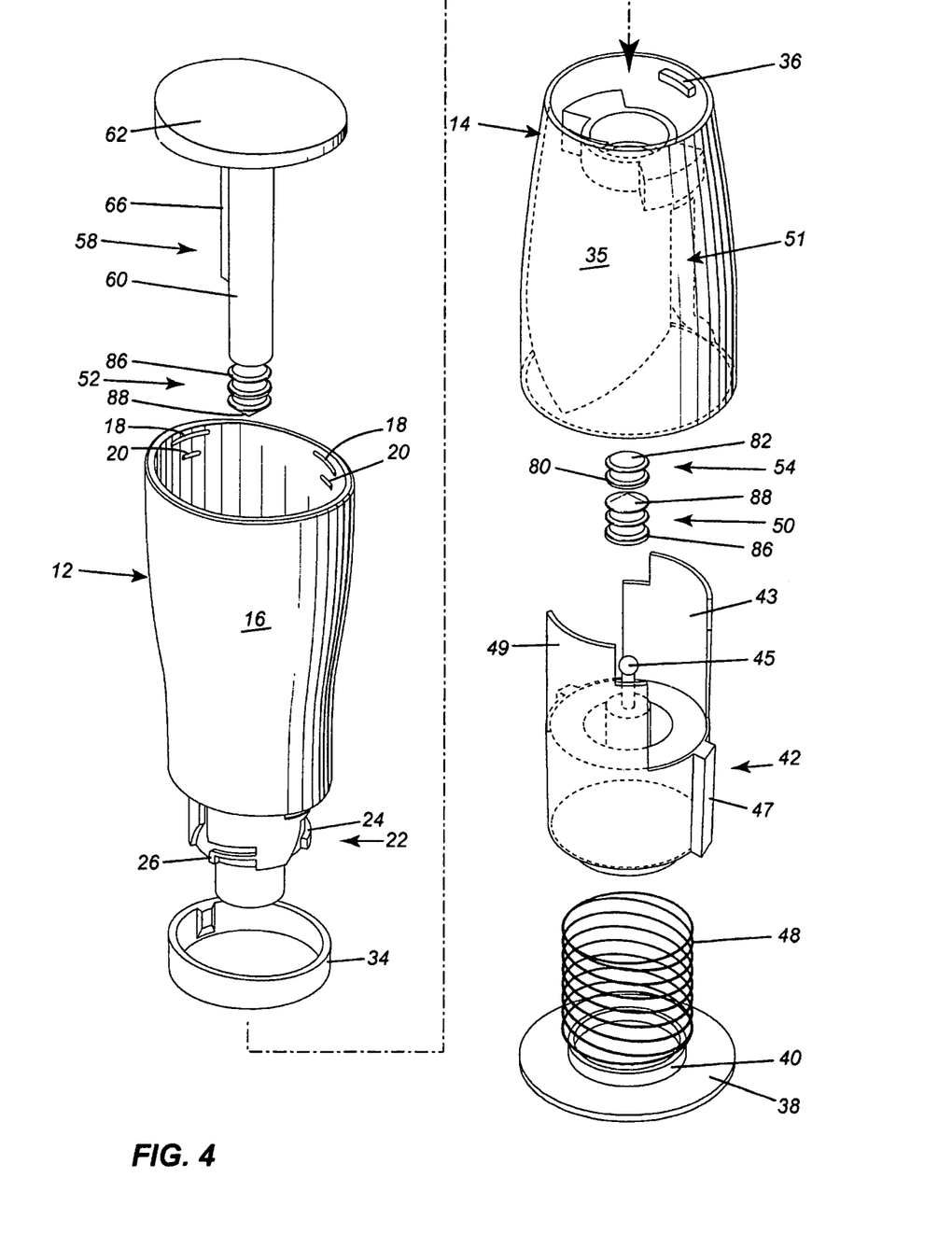
FIG. 4 is an exploded view of the reconstitution device.
Figure 5:
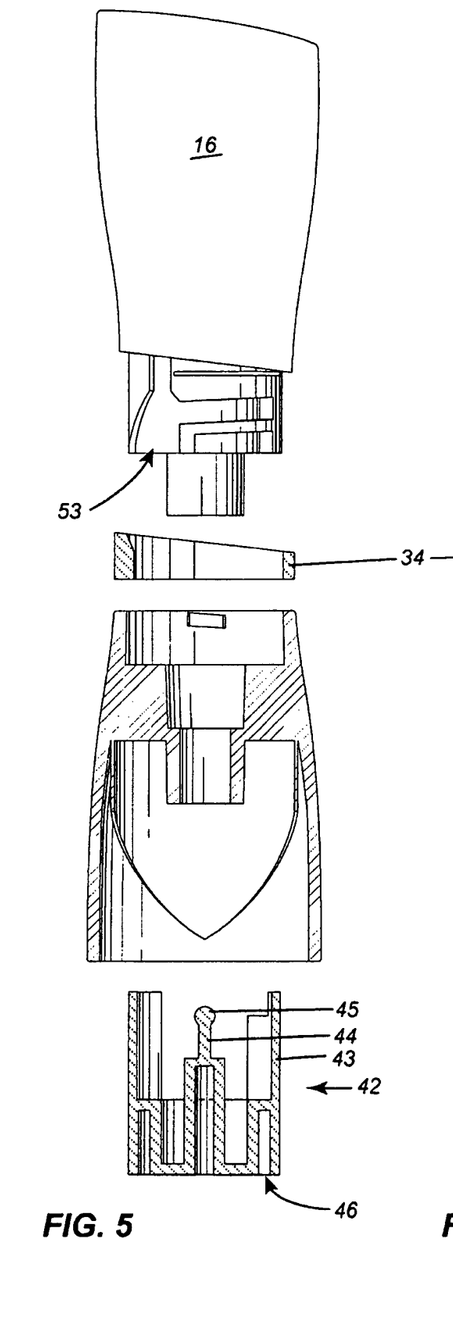
FIG. 5 is a cross sectional view of a lower portion of the reconstitution device.
Figure 6:
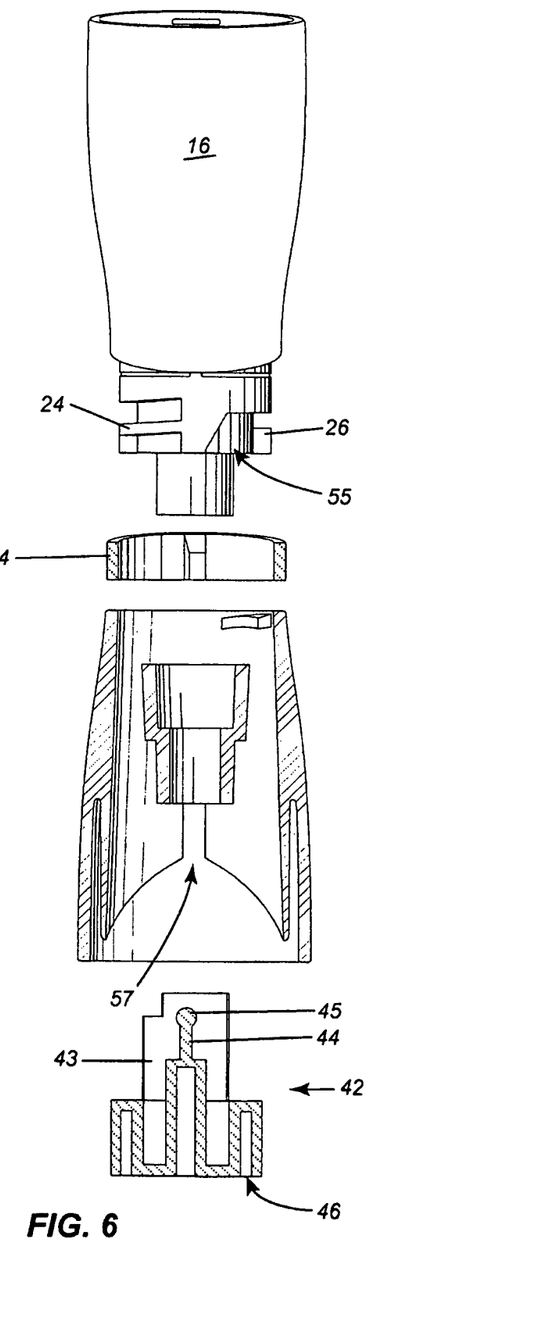
FIG. 6 is a cross sectional view similar to FIG. 4 but rotated through 90 degrees.
Figure 7:
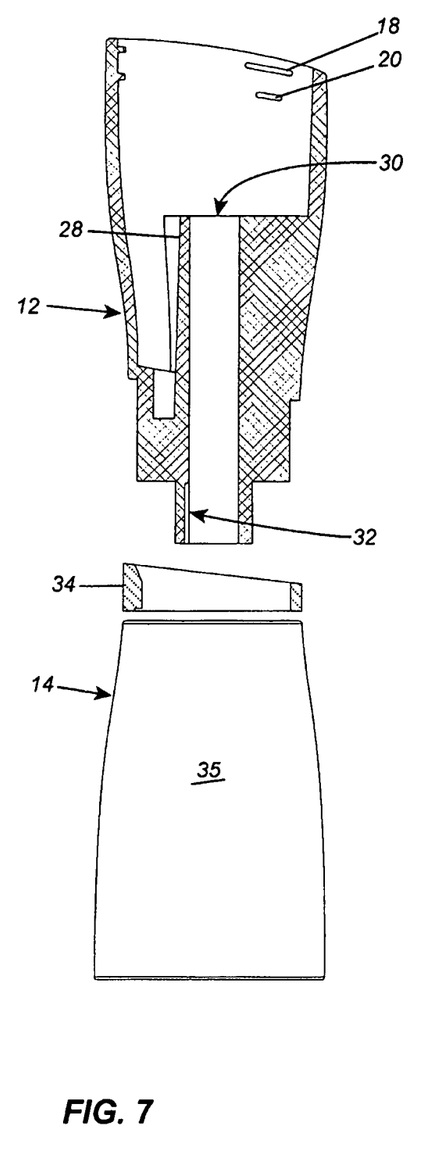
FIG. 7 is a cross sectional view of the upper portion of the reconstitution device.
Figure 8:
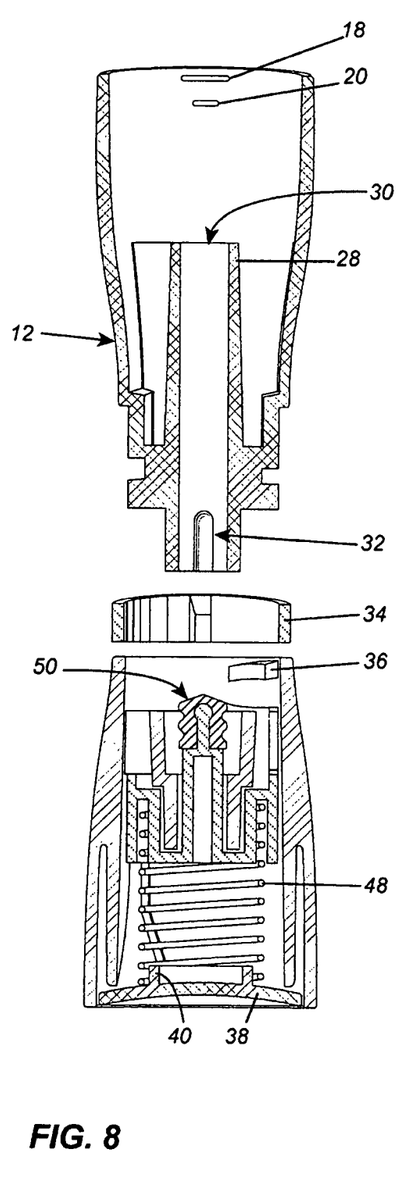
FIG. 8 is a cross sectional and exploded view of both housings forming the reconstitution device.

Referring to FIG. 1, an embodiment of a reconstitution device 10 includes a first housing generally designated by reference numeral 12 and a second housing generally designated by reference numeral 14. First housing 12 includes a wall 16, wall 16 having first projections 18 located at a first distance from the top thereof and second projections 20 at a second distance from the top thereof. In the illustrated embodiment, there are provided two such projections 18 and 20; it will be understood that in alternative embodiments, one or more is utilized.

At a narrower end 22 of first housing 12, there is provided a pair of screw threads 24, 26 for reasons which will become apparent hereinbelow. Narrower end 22 also defines first and second recesses 53, 55 intermediate screw threads 24, 26.

A conduit 28 is located interiorly of first housing 12 and includes an internal passageway 30 extending therethrough. A shearing recess 32 is provided within the interior wall of conduit 28.

A ring member generally designated by reference numeral 34 mounts over narrower end 22 of first housing 12.

On a wall 35 of second housing 14, there are provided a set of lugs 36 which act as threads for engaging with screw threads 24, 26. An end cover 38 covers the larger end of second housing 14 and is secured thereto by adhesives or welding or the like. End cover 38 includes a centering structure 40.

Mounted interiorly of second housing 14 is a moveable member 42. As may be seen in the drawings, moveable member 42 is provided with a center post 44 having an enlarged portion 45. Moveable member 42 has a spring recess 46 formed therein to receive a spring 48. At the other end, spring 48 is mounted around centering structure 40. Moveable member 42 also has a guide rib 47. Guide rib 47 is designed to fit within a channel 51 formed in an inner wall 57 of second housing 14. Moveable member 42 also has first and second legs 43, 49 extending upwardly therefrom. In an initial position, legs 43, 49 fit within recesses 53 and 55 which will then block relative rotation of housings 12, 14 with respect to each other. Thus, the housings cannot be easily unscrewed until moveable member 42 is moved out of position.

Reconstitution device 10 includes a first plunger 50 which is situated near the dispensing end of conduit 28. A second plunger 52 is located rearwardly towards the inlet end of conduit 28 while a third plunger 54 is situated therebetween. It will be noted that first plunger 50 has a recess 56 to receive center post 44 of moveable member 42.

Third plunger 54 has a side wall 80 with a concave structure. A first end wall 82 is relatively flat or planar while end wall 84 has a somewhat conical configuration. First plunger 50 has a side wall 86 with a plurality of concave recesses therein and end wall 88 (which faces third plunger 54) has a conical configuration. Similarly, second plunger 52 also has a pair of concave recesses formed therein and an end wall 92 which is somewhat conical in configuration.

A plunger rod generally designated by reference numeral 58 is situated within conduit 28. Plunger rod 58 includes a stem portion 60 which abuts second plunger 52 and a head 62 which fills the open end of first housing 12. Head 62 has at least one aperture 64 which are designed to receive or engage first projections 18. In some embodiments, the device contains two recesses or more than two recesses. Stem 60 also has a rib 66 which functions as a guide for the movement of plunger rod 58 and which engages in a slot formed in conduit 28.

The first and third plungers define therebetween a first compartment 74 while second and third plungers define therebetween a second compartment 76.

Within first compartment 74, there is provided a first component 70. In one embodiment, the first component 70 is in the form of a powder, paste or other fluid. Second compartment 76 contains a second component 72 which typically will be a less viscous material such as a liquid. Both compartments 74 and 76 are thus sealed from any contamination.

Figures 9, 10:
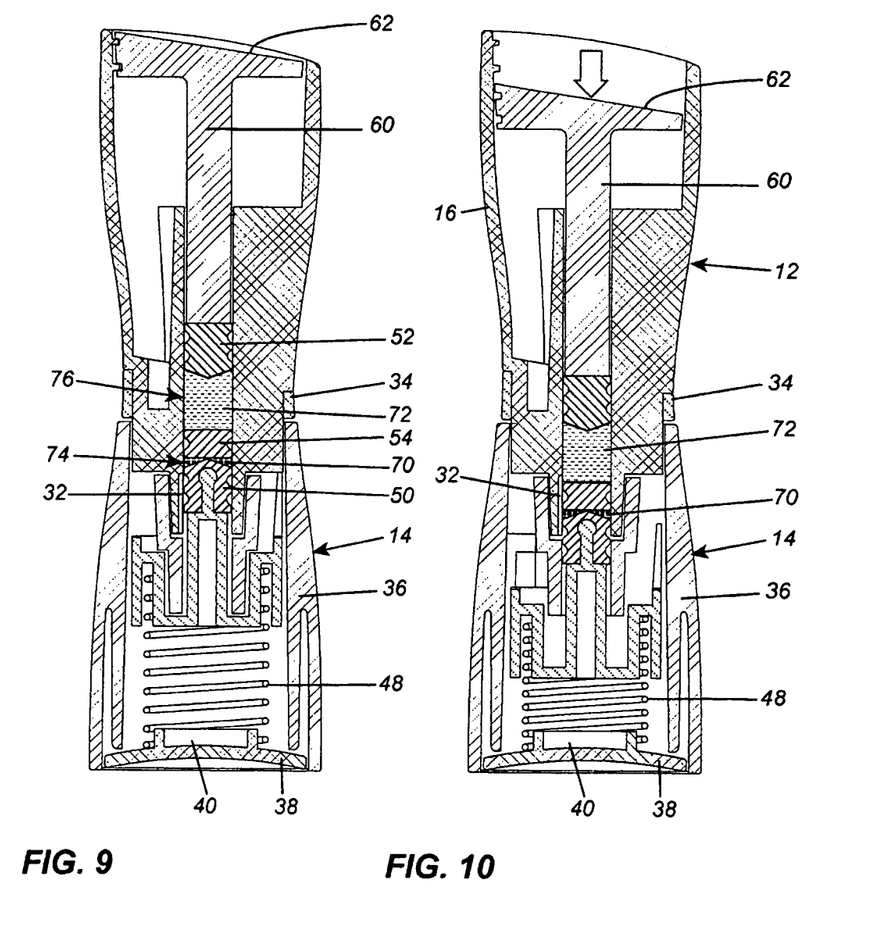
FIG. 9 is cross sectional view illustrating the assembled reconstitution device.
FIG. 10 is a cross sectional view similar to FIG. 8 illustrating commencement of the reconstitution constituting step.
Figure 11:
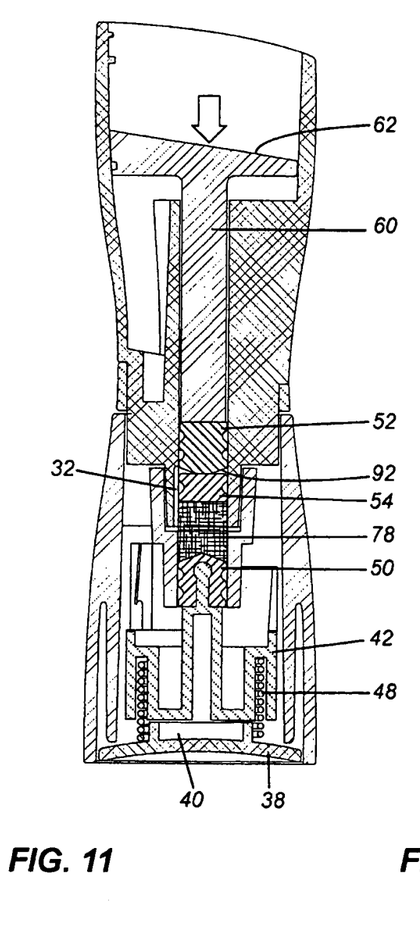
FIGS. 11 to 14 are cross sectional views illustrating the functioning of the reconstitution device.
Figure 12:
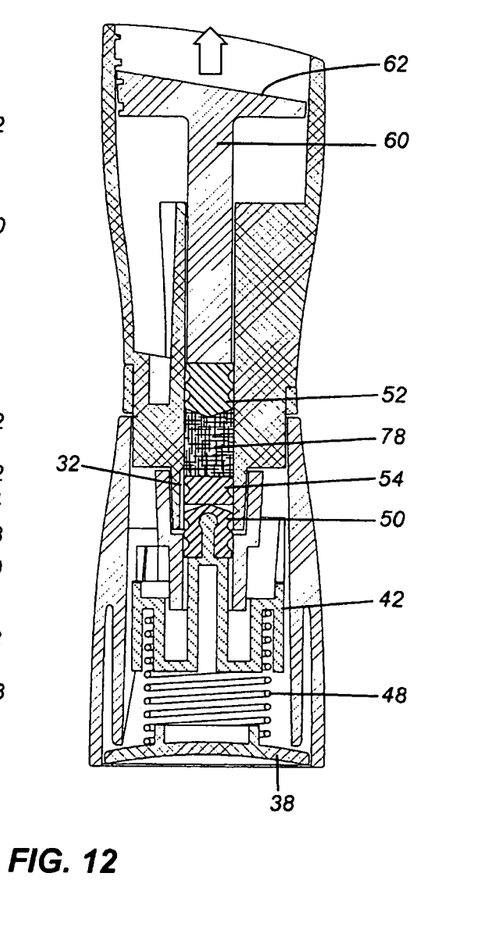
Figure 13:
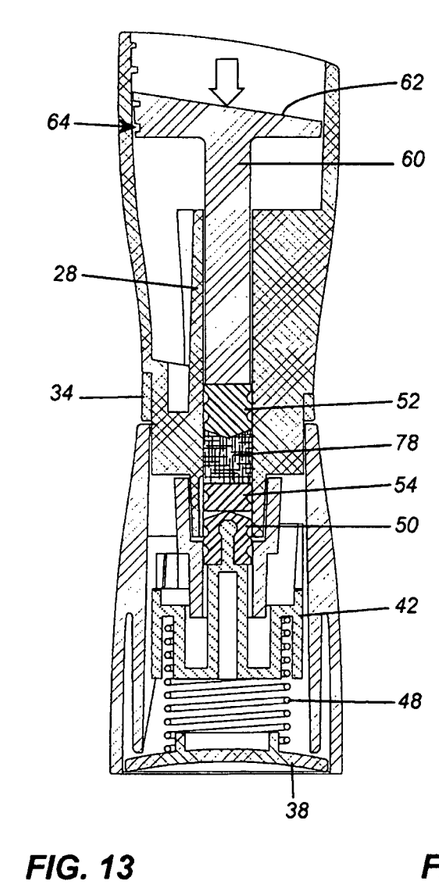
Figure 14:
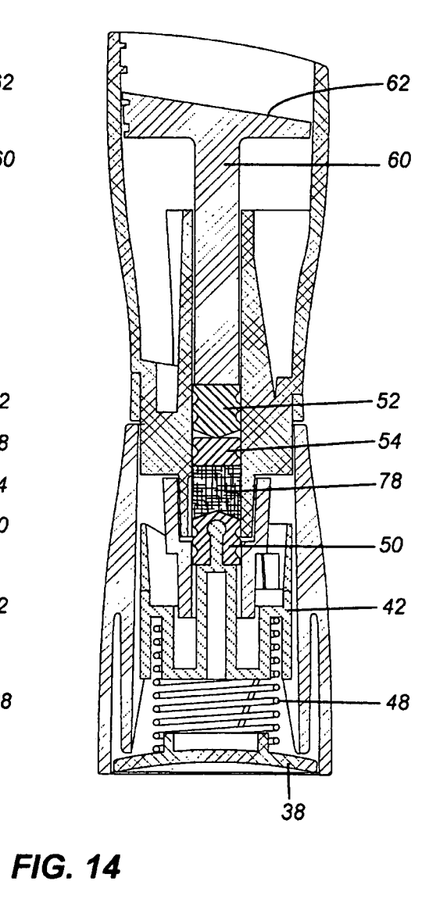
Figure 15:
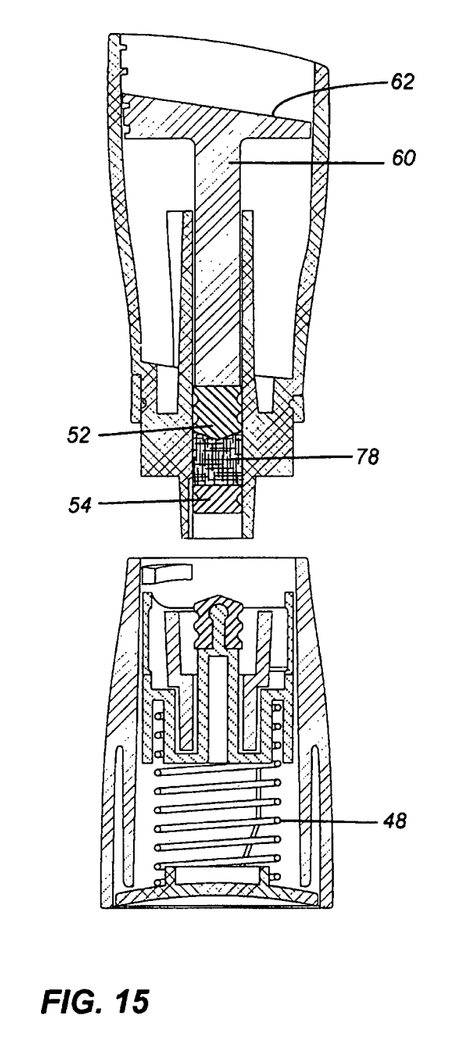
FIGS. 15 and 16 are cross sectional views illustrating the separating of the two housings for application of the contents.

As shown in FIG. 9, pressure on plunger rod 58 will cause movement of second plunger 52 and third plunger 54. Third plunger 54 will advance to a point such that shearing recess 32 is aligned with both first compartment 74 and second compartment 76 permitting a mixture 78 to be formed. The initial movement of plunger rod 58 will cause moveable member 42 to move out of its position blocking rotation of housings 12, 14. After removal of the pressure, as shown in FIG. 11, spring 48 will exert pressure on moveable member 42 which in turn will drive second plunger 52 rearwardly or upwardly as shown in the drawing. The mixture 78 will then flow back into second compartment 76. A continuing back and forth movement is exerted such that continued passage through shearing recess 32 will ensure adequate mixing of the composition 78. The spring 48 will not cause moveable member 42 to return to its original position due to projection 20.

After repeating the steps for the desired number of times, first housing 12 and second housing 14 are separated and mixture 78 is exposed for use.

Figure 16:
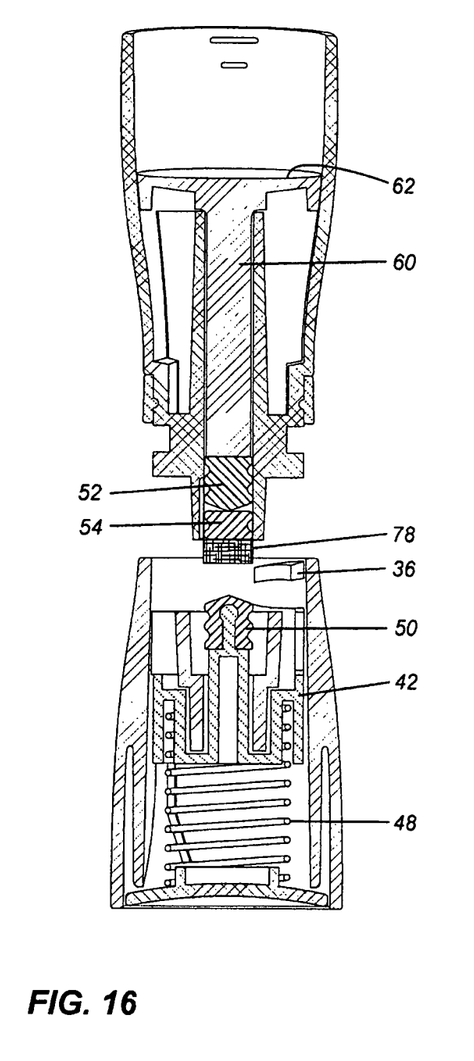
Figure 17:
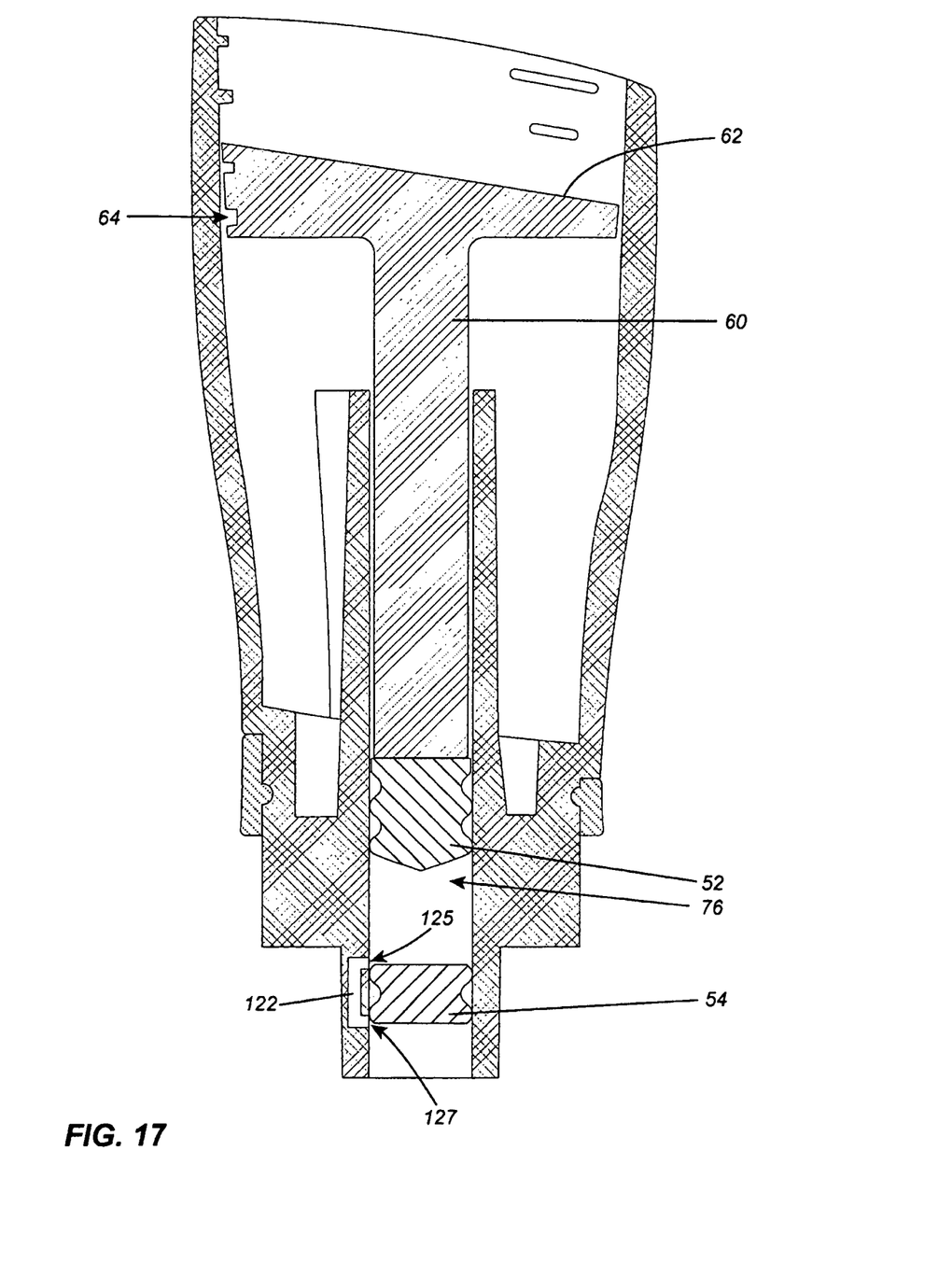
FIG. 17 is a cross sectional view of one of the housings showing an alternative embodiment.

In the embodiment of FIG. 16, there is provided a different type of shearing channel 122. As will be noted, shearing channel 122 is formed within the wall defining conduit 28. Thus, third plunger 54 will abut the wall and is sized such that there is provided an inlet 125 and an outlet 127 from shearing channel 122. When the mixing flow is reversed, the mixture enters outlet 127 and exits inlet 125.

In addition to the embodiment described above, alternate embodiments are contemplated. For example, a plunger need not be used as a means for forcing flow or mixing of compositions held within. Therefore, as one skilled in the art would appreciate, other embodiment use other types of mechanisms to cause a composition to flow out of or into a compartment. For example, in an alternative embodiment, the walls of the conduit are compressed, causing the available volume in a compartment to decrease, and thus causing a composition contained within to flow out of the compartment. Accordingly, if the walls of the conduit are expanded outward, causing the internal volume to increase and creating a relative lower pressure, composition contained elsewhere in the device is forced to flow into the compartment. In such case, the conduct is made of a flexible and durable plastic.

Alternatively, the compartment has walls that are separate from the conduit, and in such case, the compartment is a distinct chamber. For the purposes of this disclosure, compartment and chamber may be used interchangeably to describe various embodiments.

In one embodiment, the conduit and or the chambers that form the areas for mixing is at least one removable and disposable component of the device. These components, which include chambers, plungers, shearing channels, or other components, described herein, are be pre-filled with the desired compositions for mixing and administration. Therefore, in one embodiment, the device is reusable and chambers with compositions are in the form of disposable cartridges. Active ingredients and other compositions to the final pharmaceutical composition are stored in one or more pre-packaged cartridges. As noted above, such cartridges serve as chambers themselves or be inserted into chambers in certain embodiments. In such an embodiment, plungers, conduits, and other components for mixing are part of the one or more disposable cartridges.

When a composition is a chamber in subject to settling or separation, pre-mixing in a single chamber prior to combining the composition with the other chambers is desired. In such a case, as one skilled in the art would appreciate, alternative embodiments use different means of mixing, such as one of the means described herein.

Although the embodiment illustrated in the figures includes compartments shown as being separated by a plunger, alternative embodiments use different means of separation, such as a door, wall, or permeable membrane. In the case of a wall, one embodiment includes a separation device in the shearing channel, which opens for mixing. In some embodiments, more than one conduit is used. One such embodiment uses two conduits to mix two compositions separately, which are then combined prior to or at the time of dispensing. In an alternative embodiment, the two conduits are dispensed through separate openings in the device or through the same opening but in separate steps.

The coil spring, illustrated and described herein, is not the only contemplated embodiment. Other mechanical (including electronically powered) components are used to facilitate mixing in alternative embodiments. For example, one embodiment has a mechanical crank or motor. In an embodiment containing a motor, a battery is used; it should be noted, however, that a motor need not be present in the device for a battery to be included. A battery is desired for some embodiments because it allows for additional components to be included in the device.

Contemplated components include: sensors to measure the temperature, pH, viscosity, and/or other physical and chemical properties; external electronic displays; heating and/or cooling component(s); microprocessors, transmitters, and other electrical components; and/or values.

A heating or cooling component provides for two additional utilities. First, in one embodiment, the heating and/or cooling component aids in the storage of a composition in at least one chamber by providing temperature modification, notification, and/or control. Second, in another embodiment or combined with the previous embodiment, the heating and/or cooling component is used as a thermodynamic catalyst for reactions in one or more chambers. In one embodiment, the heating and/or cooling component is electrically powered or chemically facilitated. In one embodiment, one or more valves is desired or necessary to achieve a desired result because of changes in pressure before, during, or after the mixing of one or more compositions. In one embodiment, such a valve is a one way valve, capable of releasing gases resulting from mixing.

In some embodiments, compositions are stored at a pressure above or below atmospheric pressure. In one embodiment, one or more chambers fill with air. In other embodiments, one or more chambers contain a gas at above atmospheric pressure or below atmospheric pressure.

The second plunger need not be the only means of blocking passage through the shearing channel prior to activation by a user. In an alternative embodiment, the wall of the conduit has a door that is connected to the compression systems, the plungers and springs for example, that simultaneously opens the shearing channel upon initiation by a device user. In addition, in some embodiments, a third composition is stored in the shearing channel. As one skilled in the art would appreciate, one embodiment contains a shearing channel where the mixing means is one or a combination means of mixing, depending on the desired result. For example, the shearing channel may create vortex flow or utilize baffles and other protruding mixing members. In another example, the shearing channel is replaced, by other mixing means. In one embodiment for example, the third plunger, which separated the two compartments in the illustrated embodiment, operates as to open a passage way for exchange of compositions stored in the two compartments; for instance, the third plunger pivots open upon activation of mixing by a user. In one embodiment, the disclosed device allows for high shear flow for efficient emulsification of components with a minimum or exact number of mixing cycles. Although high shear flow is desired in some instances, low shear flow may be desired. In such situations, another embodiment includes at least one shearing channel that is enlarged or a less shearing mixing means is used.

Depending on the compositions being mixed, the number of cycles varies in alternate embodiments. In order to ensure a proper number of cycles, in some embodiments, the device includes a cycle counter and/or a component to limit the number of cycles possible for a given administration of a dosage. In an embodiment, a cycle counter includes a mechanical wheel or crank and the counter is internal with a stopping mechanism and/or contains an external readable display for the user. A component to count and/or limit the number of cycles is mechanical in one embodiment and electrical in another.

In an alternative embodiment, the upper housing is a disposable component and the lower housing is component made for repeated use. Therefore, in one embodiment, the lower housing component is the location for features such as the cycle counter, temperature monitor, battery, and other features discussed in and foreseeable from this disclosure.

In some embodiments, after a pre-determined number of cycles, a composition in a third chamber is released into the chamber(s) where mixing is occurring. More than three chambers is used in this manner in other embodiments. Therefore, where sequential reactions of multiple components are require or desired for a final composition, the device and method can achieve the desired result. In one embodiment for example, a first composition is stored in a first chamber, a second composition is stored in a second chamber, and a third composition is then stored in a third chamber. Upon initiation of mixing the first and second compositions are combined for a desired number of mixing cycles. Next, the third composition in the third chamber is combined with the already mixed first composition and second composition. This example is useful for a reaction where initial compound in the first and second compositions cause adverse reactions with the compounds in the third composition. However, upon mixing the first and second compositions, the undesired components are chemically altered via chemical reaction and therefore, no adverse reaction occurs when the third composition is mixed with the first two. In alternative embodiments, it is desired to have the product of the reaction of the first and second compositions at equilibrium prior to mixing and reacting the product with the third composition.

Because of the area of application in some instances, one embodiment includes a throttle or regulator for limiting the rate at which the composition can be dispensed from the device. For example, one embodiment is for the treatment of male sexual dysfunction calls for application of the pharmaceutical composition in the urethra. Therefore, dispensing the pharmaceutical composition at a high rate may result in a less then desired amount of pharmaceutical composition entering and penetrating the urethra due to splatter and/or off-target application.

In some embodiments, the device contains one or more components for more exact mixing. For example, hand actuated plungers, such as those disclosed in U.S. Pat. No. 4,250,755 (Kenney), are used to allow for more exact dosages. Other actuating components, electronic for example, are also contemplated and desired for other embodiments. Furthermore, more precise actuating plungers are used in the dispensing of the composition other embodiments.

In one embodiment, the device is built as one assembly; therefore, the upper and lower housing element is not separated for dispensing because there is no second housing to be separated. Instead, there is an opening that can be opened at the time for dispensing. The body and components of the device are made utilizing molding or other fabrication techniques. In one embodiment, materials for such components is rigid plastic, such as polyolefin, including polyethylene, polypropylene, and the like, suitable for injection molding, and in some embodiments the plastics are clear, translucent or opaque. In the case of clear or translucent material, compositions that are subject to color change or physical property change due to spoilage is viewable by a user.

In addition to flexibility in the dimensions of the device, some embodiments of the device are designed for better application, and included additional components such as nozzles or adapters. Such nozzles or adapter are be suitable for delivery of the pharmaceutical composition onto or into the body, including the urethra, the vagina, the ear and the eye, the mouth, but delivery is not limited to those parts expressly listed here. In one such embodiment, the device includes a suitable conical nozzle for administration of a pharmaceutical composition for the treatment of male sexual dysfunction into the urethra of a subject. In another embodiment, the device includes a suitable conical nozzle for administration of a pharmaceutical composition for the treatment of female sexual dysfunction into the vagina of a subject.

We claim:
1. A device for mixing a first component with a second component, said device comprising:
first and second housings (12, 14);
said first and second housing (12, 14) each having a partial screw thread (24, 26,38) formed on an exterior surface thereof, said first and second housings (12, 14) being engageable together by means of said screw threads (24, 26,38);

a conduit (28) having an internal passageway (30) formed in said first housing, said internal passageway (30) having a dispensing end and an inlet end;

a first plunger (50) mounted in said internal passageway (30) proximate said dispensing end;

a second plunger (52) mounted in said internal passageway proximate (30) said inlet end;

a third plunger (54) mounted in said internal passageway intermediate said first and second plungers (50, 52), said first and third (50, 54) plungers defining a first compartment (74) therebetween, said second and third plungers (52, 54) defining a second compartment (76) therebetween;

a plunger rod (58) at least partially within said internal passageway at said inlet end;

a moveable member (42) located in said second housing, said moveable member engaging said first plunger, said moveable member (42) having at least one leg (43, 49) extending upwardly therefrom, said upwardly extending leg (43, 49) engaging said first housing (12) such that said first and second housing cannot be disengaged from an initial first position, the arrangement being such that when said plunger rod is moved to commence transfer from said second compartment (76) to said first compartment (74), said leg (43,49) on said moveable member disengages from said first housing (12) to permit rotatable movement of said first and second housings (12, 14).

2. A reconstitution device comprising:
a device (10) suitable for mixing a first component (70) with a second component (72), said device comprising: first and second housings (12, 14);

said first and second housings (12, 14) being non-movably engageable together;

a conduit (28) having an internal passageway (30) formed in said first housing (12), said internal passageway having a dispensing end and an inlet end;

a first plunger (50) mounted in said internal passageway (30) proximate said dispensing end;

a second plunger (52) mounted in said internal passageway (30) proximate said inlet end;

a third plunger (54) mounted in said internal passageway (30) intermediate said first and second plungers (50, 52), said first and third plungers (50, 54) defining a first compartment (74) therebetween, said second and third plungers (52, 54) defining a second compartment (76) therebeween;

a plunger rod (58) at least partially within said internal passageway (30) at said inlet end;

a moveable member (42) located in said second housing (14); said moveable member (42) engaging said first plunger (50); and a shearing channel (32) formed in a side wall of said conduit (28) to permit mixing of contents located in said first and second compartments (74, 76).

3. The device of claim 2 further including a spring member (48) mounted in said second housing (14) biasing said moveable member (42).

4. The device of claim 3 wherein said plunger rod (58) has a generally T shaped configuration with a shaft (60) designed to engage said second plunger (52) and an enlarged head (62) for pushing said plunger rod, said enlarged head (62) having at least one recess (64) in a side wall thereof for engaging said first projection (18).

5. The device of claim 2 wherein said first and second housings (12, 14) are screwthreadably engageable (24, 26, 36).

6. The device of claim 5 wherein both of said first and second plungers (50, 52) have one end wall (88, 92) of a conical configuration.

7. The device of claim 2 wherein said first housing (12) has first and second projections (18, 20) formed on an inner facing wall of said housing, said first projection (18) being designed to retain said plunger rod (58) in a first desired position and said second projection (20) being designed to prevent passage of said plunger rod (58) after use.

8. The device of claim 2 wherein said second housing (14) includes a base (38) said base (38) having a structure (40) to center and retain said spring member (48) in position.

9. The device of claim 2 wherein said moveable member (42) has a rod structure (48) to engage and retain said first plunger (50) thereon.

10. The device of claim 2 wherein said third plunger (54) has a side wall (80) and a pair of end walls (82, 84), said side wall (80) having a concave configuration, both of said end walls (82, 84) having a relatively flat surface.

11. The device of claim 2 further including a ring member (34), said ring member (34) extending about a point of joinder of said first and second housing (12, 14).

12. The device of claim 2 wherein said moveable member (42) has a cavity (46) formed therein, said cavity (46) being designed to receive one end of said spring member (48).

13. The device of claim 2 wherein said moveable member has a pair of legs extending outwardly therefrom, said legs engaging with said first housing between said screw threads to thereby prevent relative rotation of said first and second housings when in an initial position.

14. The device of claim 2 wherein said moveable member (42) includes a rib on an outer surface thereof, said second housing having an inner housing secured thereto, said inner housing having a channel therein to receive said rib.

* * * * *